US012599651B2

(12) United States Patent
Fahy et al.

(10) Patent No.: US 12,599,651 B2
(45) Date of Patent: Apr. 14, 2026

(54) PHARMACEUTICALS AND DOSING MEANS FOR HUMAN AGING REVERSAL

(71) Applicant: INTERVENE IMMUNE INC., Manhattan Beach, CA (US)

(72) Inventors: Gregory Fahy, Norco, CA (US); Robert Brooke, Manhattan Beach, CA (US)

(73) Assignee: INTERVENE IMMUNE INC., Manhattan Beach, CA (US)

( * ) Notice: Subject to any disclaimer, the term of this patent is extended or adjusted under 35 U.S.C. 154(b) by 0 days.

(21) Appl. No.: 18/346,365

(22) Filed: Jul. 3, 2023

(65) Prior Publication Data

US 2024/0299502 A1 Sep. 12, 2024

Related U.S. Application Data

(62) Division of application No. 16/637,502, filed as application No. PCT/US2018/045684 on Aug. 7, 2018, now Pat. No. 11,730,795.

(60) Provisional application No. 62/543,269, filed on Aug. 9, 2017.

(51) Int. Cl.
| | |
|---|---|
| *A61K 38/27* | (2006.01) |
| *A61K 31/155* | (2006.01) |
| *A61K 31/5685* | (2006.01) |
| *A61K 45/06* | (2006.01) |
| *C07K 14/61* | (2006.01) |

(52) U.S. Cl.
CPC .......... *A61K 38/27* (2013.01); *A61K 31/5685* (2013.01)

(58) Field of Classification Search
CPC .............. A61K 2300/00; A61K 31/155; A61K 31/5685; A61K 38/27; A61K 45/06; C07K 14/61
See application file for complete search history.

(56) References Cited

U.S. PATENT DOCUMENTS

| | | | |
|---|---|---|---|
| 5,855,920 A | 1/1999 | Chein | |
| 2008/0194553 A1* | 8/2008 | Gillessen | ................ A61P 43/00 |
| | | | 514/367 |
| 2012/0071349 A1* | 3/2012 | Qi | ............................ A61P 5/10 |
| | | | 506/10 |
| 2017/0027914 A1 | 2/2017 | Qi | |

OTHER PUBLICATIONS

Walker RF., "Sermorelin: A better approach to management of adult-onset growth hormone insufficiency?" Clinical Interventions in Aging, 2006, I(4): 307-308. (Year: 2006).*
International Search Report and Opinion Issued on Nov. 23, 2018 in connection with corresponding International Application Serial No. PCT/US2018/045684.
Fahy "Reversal of epigenetic aging and immunosenescent trends in humans" Aging Cell, 2019, pp. 1-12 (2019).

* cited by examiner

*Primary Examiner* — Julie Ha
(74) *Attorney, Agent, or Firm* — Arrigo, Lee, Guttman & Mouta-Bellum, LLP; Carla Mouta-Bellum

(57) ABSTRACT

A combination of medications and medication doses is disclosed whereby age-related changes in systemic inflammation, cancer risk, heart disease risk, CD38 expression, hair color, thymotrophic hormones, immune cell populations, the CD4/CD8 cell ratio, bone marrow density, thymus structure, kidney function, and epigenetic age can be reversed in humans. Surprisingly, agents that accelerate the growth of cells reduce cancer risk, agents that intensify immune responses attenuate age-related inflammation, agents with no prior connection to hair color reverse age-related hair whitening, and a combination of agents that induces IGF-1, a hormone previously thought to drive systemic aging, results in a reversal of systemic aging as documented by an epigenetic clock. Medication combinations useful in the present invention include human growth hormone (GH) or GH releasers, dehydroepiandrosterone (DHEA), and metformin.

11 Claims, 12 Drawing Sheets

Figure 4.

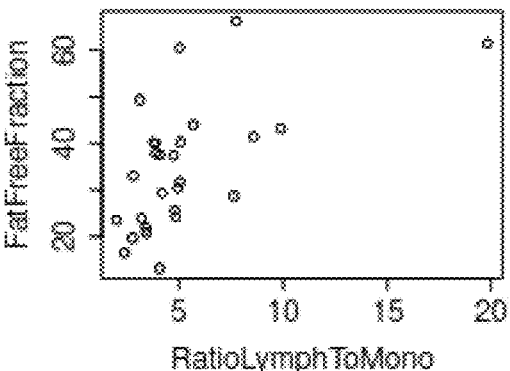

shows the relationship between thymic fat-free fraction (TFFF; see below) and the lymphocyte
to monocyte cell ratio (LMR).   The statistical significance of the correlation is at the p=0.0019 level, and
links the improvement in LMR to the improvement in putative thymic functional mass.  In fact, when
variance explained by changes in TFFF are factored out of variance in the LMR, no change in LMR
survives, suggesting that changes in the LMR are in fact caused by improvements in thymic function.

Figure 5.

To our surprise, three of our trial volunteers (33%) reported to us that their wives and friends had noticed darkening of their hair. Figure 5 provides evidence that the invention surprisingly reverses the aging of hair follicles, based on three before-and-after comparisons showing one volunteer's hair a few months before treatment and at the end of treatment. This result is all the more remarkable considering that hair whitening is caused by the death of follicular melanocyte stem cells, suggesting restoration of stem cells by the invention.

These observations were completely unanticipated. This phenomenon is suggestive of a broad "anti-aging" effect, and has not been reported to our knowledge after use of any of the individual agents of the present invention (in this case, GH, DHEA, and metformin) when they are not combined with one another as required by the present invention, and this effect of the combination is unpredictable from the properties of the uncombined agents. The phenomenon adds further market appeal to the treatment, manufacturing process, medication combination, and compositions of the present invention.

Figure 6.

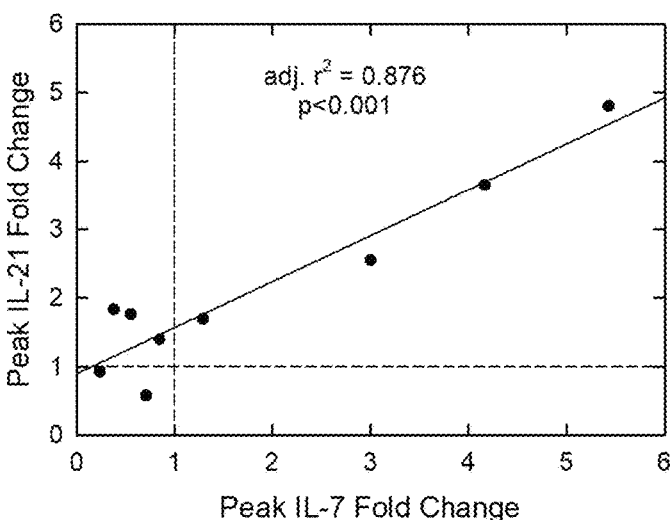

provides evidence that the invention surprisingly restores thymotrophic hormones in a subset of TRIIM trial volunteers, based on correlated increases in both IL-7 and IL-21 (FGF-21) in these men. IL-7 is a hormone whose downregulation in youth has been associated with the onset of thymic involution, and restoration of which has been proposed, but not achieved, for inducing thymic regeneration [5]. IL-21 has been shown to regenerate the aged thymus in rodents when excessively over-expressed to a level that may or may not be feasible or desirable in humans [2, 47], and is a theoretical alternative pathway to thymus regeneration. We asked whether part of the mechanism of action of our invention was induction of IL-7 and/or IL-21, i.e., stimulation by our medication combination of endogenous thymic regeneration pathways. Figure 6 indicates that the answer to the question is positive, and demonstrates a heretofore unknown and safe method for increasing IL-7 and IL-21 in humans. Once again, reactivation of pathways found in youth provides additional evidence for an overall aging reversal effect of our combination of medications.

Figure 7.

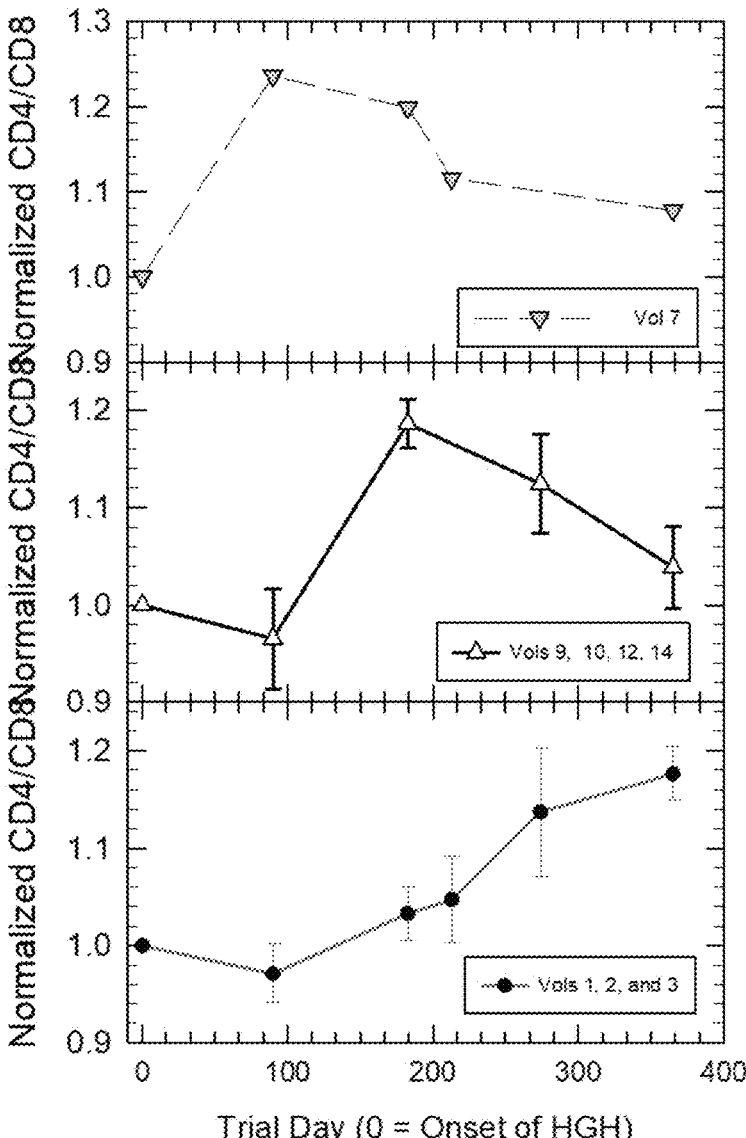

Trial Day (0 = Onset of HGH)

reveals a heretofore unknown phenomenon, i.e., that the CD4/CD8 cell ratio peaks in the face of a constant or an increasing dose of GH or rise in IGF-1, and thereafter declines. Different men show a peak in CD4/CD8 ratio at different times (here, 3, 6-9, and 12 months; one volunteer failed to respond at any time). The decline of CD4/CD8 cell ratio with aging is a classical indication of the "immune risk phenotype" or immunosenescence, and appears to occur with or without chronic viral exposure [24] and has been a strong predictor of the short-term risk of death [37]. Our results therefore indicate that prior art methods of regenerating the thymus require improvement. Without knowledge of the

Figure 8.

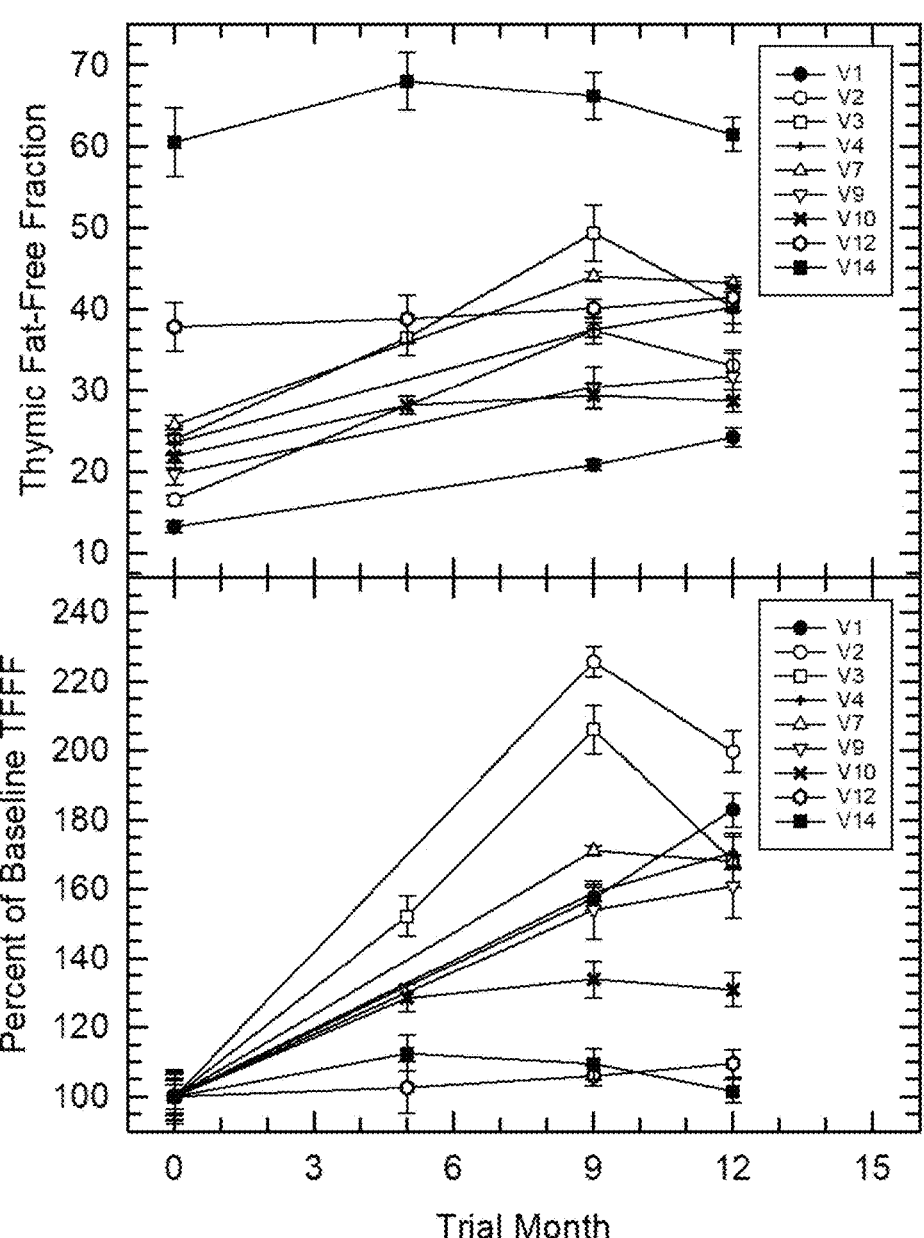

provides detailed information on the improvement in functional thymic mass achieved by the TRIIM trial protocol and medications, as inferred from a reduction in the thymic fat percentage (TFFF = thymic fat-free fraction = 100 minus the percentage of thymic mass represented by fat, where the thymic fat fraction was computed using an algorithm that has been shown to be of higher accuracy than bone marrow consistent with this requirement. This change is one more change that is contrary to the direction of normal aging trends.

Figure 10.

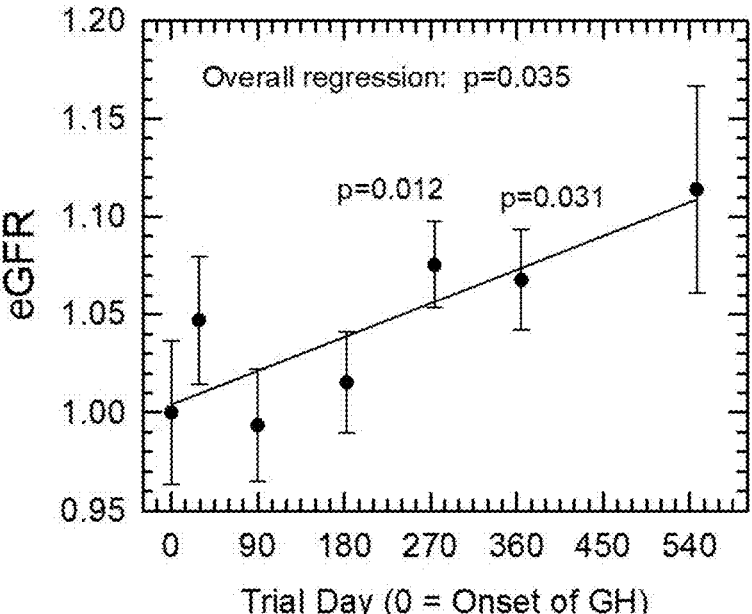

shows that the medications and treatments of the present invention result in increased glomerular filtration rates over the course of the 12 months of treatment and beyond, reaching statistical significance at 9 months, 12 months and overall out to 18 months. "eGFR" is "estimated GFR" and is calculated based on age, sex, race, and serum creatinine levels. Normally, renal function declines with aging. Here is another example of the functional reversal of a normal age-related trend.

Figure 11.

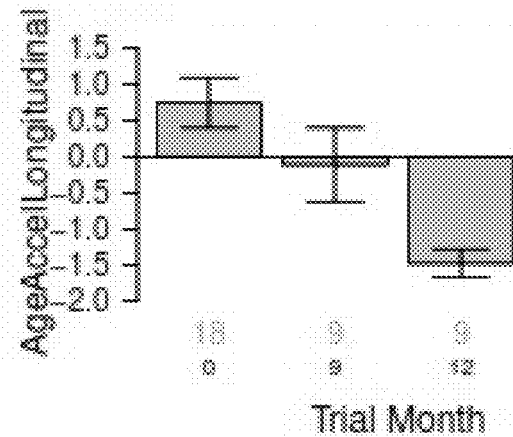

demonstrates the first direct evidence for a global reversal of human aging.  Using an epigenetic clock licensed by Zymo Research [20], the longitudinal epigenetic age of TRIIM trial volunteers was calculated at months 0, 9, and 12.  At baseline (month 0), the mean epigenetic age of the volunteers was about 0.75 years older than their chronological ages.  By 9 months, there was a gain of about 0.8 years, indicating rejuvenation back to a biological age appropriate for the volunteers' mean chronological age.  However, three months later, the mean epigenetic age had declined to 1.5 years younger than the volunteers' mean chronological age.  In total, net rejuvenation after 1 year of treatment was about 2.25 years.  But since 1 year of treatment would have normally entailed one additional year of aging, the net gain was actually 3.25 years compared to no treatment.  The p value for this change was 0.0059.  In general, epigenetic clocks of this kind can determine biological age more accurately than biological age can be estimated from chronological age.

Figure 12.

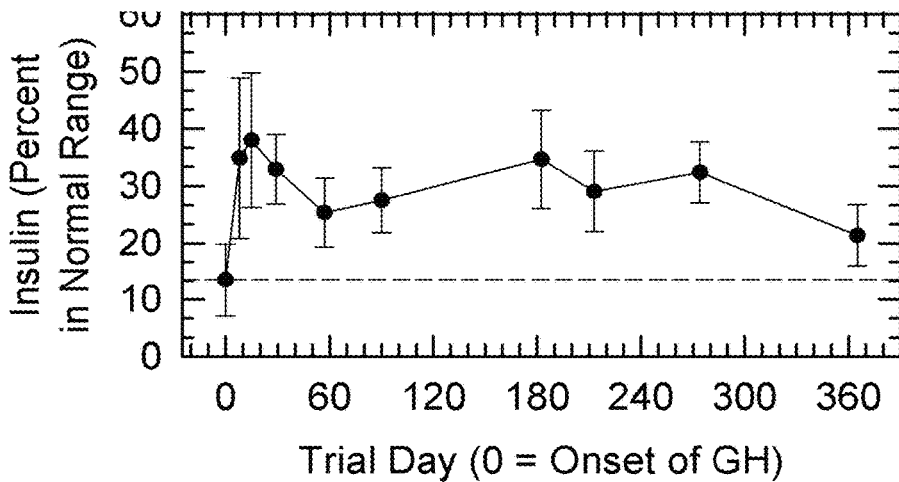

demonstrates that the invention can successfully suppress GH-induced hyperinsulinemia despite the increasing GH doses described in Figure 1. Here, for context, insulin blood levels are expressed as a fraction of the distance from the bottom of the normal range to the top of the normal range. Although insulin control was not perfect, the final increase in insulin at trial end was acceptable based on volunteers averaging about one fifth of the upper limit for insulin. Note the rise in insulin early on, as lower doses of GH were given without administration of DHEA or metformin, followed by declining insulin levels as antihyperinsulinemic therapy was begun. Insulin and the normal insulin range were as reported by Quest Diagnostics.

Summary

The present invention provides for the first time medication combinations, compositions, doses, dosage regimens, and other methods that have demonstrable and objective benefits for the treatment of immunosenescence and many fundamental aspects of aging in human patients, and for further improvements that are now enabled by the present disclosures.

Additional ways to describe the invention include the following.

1. A method whereby the co-administration of human growth hormone and/or one or more human growth hormone releasing agents, DHEA, and metformin to humans results in the reversal of age-related health risk factors other than thymic involution.

2. The method above ("the method") wherein the dose of human growth hormone or growth hormone releasing agents is adjusted in response to changes in the CD4 to CD8 T cell ratio so as to prevent the CD4 to CD8 T cell ratio from declining due to over- or under-administration of human growth hormone or growth hormone releasing agents.

PHARMACEUTICALS AND DOSING MEANS FOR HUMAN AGING REVERSAL

CROSS-REFERENCE TO RELATED APPLICATIONS

This application is a divisional application and claims the benefit of U.S. application Ser. No. 16/637,502, filed Feb. 7, 2020, which claims priority to PCT Application No. PCT/US18/45684, filed Aug. 7, 2018, which further claims priority to U.S. Provisional Application Ser. No. 62/543,269, filed on Aug. 9, 2017, all of which are incorporated herein by reference in their entireties.

BACKGROUND OF THE INVENTION

The present invention was initially motivated by the desirability of discovering medications and medication doses and methods capable of advantageously regenerating the human thymus (i.e., pharmacologically addressing the medical condition known as thymic involution) so as to prevent age-related immune dysfunction (immunosenescence) or restore immune function (reverse immunosenescence) in the elderly. We sought to correct the deficiencies of the few [12, 33, 34] prior art medications and medication doses and methods for human thymus regeneration, which have failed to adequately address the issue of insulin control, safety, and efficacy in otherwise healthy aging adults. Prior to the present invention, the following concerns and unanswered questions confronted the use of prior art medications and medication doses and methods intended to treat the medical condition known as thymic involution (i.e., to induce clinical thymus regeneration).

The Problem with Growth Hormone: Aging, Diabetes, and Cancer

Growth hormone (GH) has been the basis of attempted human thymus regeneration to date [12, 33, 34] based in part on positive short-term results in animals [25]. However, there is no approved or generally recognized benefit of GH other than to treat certain childhood diseases and failure to grow, or bona fide GH deficiencies in adults, which are quite rare. In addition, the scientific consensus is that aging itself is driven by the IGF-1 produced in response to GH secretion given the universality of the involvement of similar signaling processes in the aging of most animal species [28, 29, 43], the fact that mutant mice deficient in GH/IGF1 signaling live longer than wild-type mice [7, 19, 29, 41, 43] and that there is an inverse correlation between IGF-1 levels and lifespans between mouse strains [48].

One pro-aging effect of HGH administration is the "diabetogenic" effect of GH, wherein HGH increases insulin resistance and consequently increases blood insulin levels [30, 38]. Elevated insulin levels may lead to an increased risk of atherosclerosis, other cardiovascular diseases, and accelerated aging in general [31]. An instructive hallmark of calorie restriction, which is one of the most powerful anti-aging interventions now known, is simultaneous reduction in both glucose and insulin levels secondary to powerfully increased insulin sensitivity [4, 45]. Normal aging and GH administration both result in the opposite effect, i.e., elevated insulin and unchanged or elevated glucose levels, owing to increased insulin resistance. This phenomenon is often called metabolic syndrome or type II diabetes, and is responsible for many age-related diseases. It is undesirable to foster this condition in an attempt to slow aging, but this serious side effect of HGH administration has been almost universally ignored. Although Fahy, uniquely, proposed HGH administration in combination with dehydroepiandrosterone (DHEA) to block the diabetogenic effect of HGH [11, 12], his method was only shown to be effective in a single relatively young individual [12, 13], and its validity and sufficiency for the general population therefore remains unknown. Recently, 50 mg of DHEA per day was found to improve glucose tolerance in 65-75 year old men [46], but this was in the absence of GH administration, leaving the effectiveness of DHEA in combination with GH as well as optimal methods of DHEA use with GH unresolved. Past use of GH for thymus regeneration in HIV patients (who may be unrepresentative of the general healthy aging population [32]) ignored the issue of hyperinsulinemia [33, 34], and it is unknown whether correcting hyperinsulinemia might prevent any benefit of thymus regeneration.

GH administration to adult humans [1, 3, 18, 42] and to adult rodents [10, 23, 26] has not been shown to increase the risk of developing cancer despite often elevating IGF-1 levels to far above the normal range. However, paradoxically, the highest levels of IGF-1 in men not treated with HGH have been associated with about a 50% increase in prostate cancer risk [36], and in women, IGF-1 stimulates processes that worsen breast cancer outcomes [9]. Therefore, there has been an unresolved concern that use of growth hormone for thymus regeneration may lead to significant elevations in cancer risk. Moreover, DHEA is a precursor to testosterone, and androgens are a risk factor for prostate cancer development and progression [39]. Therefore, the combination of DHEA and HGH is particularly concerning from the standpoint of potential exacerbation of prostate cancer, and it might be argued that the decline of DHEA with age [40, 44], like the decline of GH secretion and IGF-1 levels with age, has arisen as a hedge against cancer. Furthermore, sex hormones, including androgens, have been shown to drive thymus involution [16, 17], making the use of DHEA in a treatment for thymus regeneration potentially counterproductive.

Thymus Regeneration vs "Inflammaging"

In addition to increased insulin resistance, another major hallmark of aging is "inflammaging" [14], which is a state of chronic and generalized inflammation that arises in the course of normal aging and has been speculated to contribute to age-related increases in cancer risk. It is logical to assume that if thymus regeneration were to increase the intensity of immune responses in the elderly, this would exacerbate inflammaging, and in fact, one famed gerontologist and immunologist to whom thymus regeneration was suggested by one of the present inventors (G.M.F.) did strongly express just this concern. A priori, there is no way to rebut this concern or determine the magnitude of this presumed problem, and the prior art is completely silent on this question; although HGH has been widely used, its potential exacerbation of inflammaging has not been defined. To underscore the seriousness of this potential drawback, it was recently reported that a new immune system stimulating drug, TGN-1412, induced a severe inflammatory reaction known as a "cytokine storm" in a Phase 1 trial, and therefore had to have its development halted [6]. Furthermore, the thymus involutes early in life in all vertebrates, including humans, leading some researchers to question if this change is adaptive, perhaps, for example, to blunt inflammation later in life. If so, thymus regeneration could be counterproductive.

In order to address these unknowns, a first of its kind one-year clinical trial was carried out on 9 healthy men aged 50-65. The results have been illuminating, not only with respect to the above-described questions, but also as to the existence of previously unknown deficiencies of prior art methods as well as the effectiveness of a new pharmaceutical dosage form that provides an unprecedented set of new health benefits and valuable new drug indications. These indications go beyond the immediate goals of thymus regeneration and T cell improvement. The same essential pharmacological approach should be effective as well in women.

SUMMARY OF THE INVENTION

The invention is a drug combination and mode of drug administration that has novel therapeutic effects that are consistent with a generalized reversal of human aging. The invention is also the first demonstrated method for reversing multiple aspects of aging, and even aging in general, in humans. More specifically, the invention consists of a combination of human growth hormone (GH) and/or GH releasers, dehydroepiandrosterone (DHEA), and metformin and means of delivering this combination of medications that results in the reversal of normal age-related changes in kidney function, systemic inflammation, cancer risk, heart disease risk, CD38 expression, hair color, thymotrophic hormones, the CD4/CD8 cell ratio, immune cell populations, bone marrow density, thymus structure, and epigenetic age. Still more specifically, the above drug combination is to be given so as to optimize the CD4/CD8 cell ratio, which, using prior art methods, cannot be correctly optimized. Still more specifically, the above drug combination is to be given so as to minimize GH-induced or GH releaser-induced hyperinsulinemia and unpleasant side effects.

The invention also comprises the use of a combination of human growth hormone (GH) and/or GH releasers with dehydroepiandrosterone (DHEA) and metformin to manufacture a pharmaceutical dosage form to treat or to prevent broad aspects of human aging, including any one of, any combination of, or all of age-related changes in systemic inflammation as indicated by hsCRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced hyperinsulinemia. The pharmaceutical dosage form or composition may consist of three separate agents or agent classes (the GH and/or GH releaser; DHEA; and metformin) administered simultaneously or within 2 hours of one another, or it may consist of GH and/or a GH releaser used simultaneously with or within two hours of a unified companion product composition containing DHEA in combination with metformin.

More particularly, in one aspect of the invention there is disclosed the use of a combination of human growth hormone (GH) and/or a GH releaser, dehydroepiandrosterone (DHEA), and metformin to manufacture a pharmaceutical dosage form to treat, prevent, or reverse broad aspects of human aging, including any one of, any combination of, or all of age-related changes in systemic inflammation as indicated by hsCRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced or GH releaser-induced hyperinsulinemia. This combination may comprise any of a) three separate agents or agent classes (the GH and/or GH releaser; DHEA; and metformin), which are to be administered simultaneously or within 2 hours of one another; and b) GH and/or a GH releaser used simultaneously with or within two hours of a unified companion product composition containing DHEA in combination with metformin.

In another aspect of the invention, there is disclosed a composition for use in the treatment of human aging, comprising a combination of GH and/or a GH releaser, dehydroepiandrosterone, and metformin whose administration results in mitigation of age-related changes in any one of, any combination of, or all of the following: systemic inflammation as indicated by hsCRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced or GH releaser-induced hyperinsulinemia. This composition may comprise any of a) three separate agents or agent classes (the GH and/or GH releaser; DHEA; and metformin), which are to be administered simultaneously or within 2 hours of one another, or b) GH and/or a GH releaser used simultaneously with or within two hours of a unified companion product composition containing DHEA in combination with metformin.

In still another aspect of the invention, there is disclosed a method for the mitigation or reversal of human aging, comprising administering a combination of GH and/or a GH releaser, dehydroepiandrosterone, and metformin so as to result in mitigation or reversal of age-related changes in any one of, any combination of, or all of the following: systemic inflammation as indicated by hsCRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced of GH releaser-induced hyperinsulinemia. This method may further comprise any of: a) administering three separate agents or agent classes (the GH and/or GH releaser; DHEA; and metformin) simultaneously or within 2 hours of one another, or b) administering GH and/or a GH releaser simultaneously with or within two hours of the oral administration of a unified companion product composition containing DHEA in combination with metformin.

In still another aspect of the invention, there is disclosed a composition for use in the treatment of human aging, comprising an agent that increases IGF-1 levels and one or more insulin-lowering agents whose administration results in mitigation of age-related changes in any one of, any combination of, or all of the following: immune system function as indicated by the lymphocyte to monocyte ratio, CD38-positive blood cell counts or percentages, total CD4 and/or CD8 T cell numbers or percentages, IL-7 levels, IL-21 levels, the CD4/CD8 cell ratio, naïve CD4 and/or CD8 cell numbers or percentages, bone marrow density, thymic density or fat-free fraction, or other accepted markers of immune system function, inflammation as indicated by hsCRP or other accepted markers, cancer risk as indicated by PSA levels, the percent of free PSA, the ratio of PSA to percent of free PSA, its reciprocal, and/or by the lymphocyte to monocyte cell ratio or other accepted markers of cancer risk, heart disease risk as indicated by the lymphocyte to monocyte cell ratio, CD38-positive blood cell counts or percentages or other accepted markers of heart disease risk, hair color, glomerular filtration or other accepted markers of kidney function, epigenetic age, or other critical endpoints of aging, as well as to reduce or prevent GH-induced or GH releaser-induced hyperinsulinemia.

Yet another aspect of the invention involves a composition for use in the treatment of human aging, comprising a combination of one or more anabolic agents with one or more insulin-lowering agents whose administration results in mitigation of age-related changes in any one of, any combination of, or all of the following: immune system function as indicated by the lymphocyte to monocyte ratio, CD38-positive blood cell counts or percentages, total CD4 and/or CD8 T cell numbers or percentages, IL-7 levels, IL-21 levels, the CD4/CD8 cell ratio, naïve CD4 and/or CD8 cell numbers or percentages, bone marrow density, thymic density or fat-free fraction, or other accepted markers of immune system function, inflammation as indicated by hsCRP or other accepted markers, cancer risk as indicated by PSA levels, the percent of free PSA, the ratio of PSA to percent of free PSA, its reciprocal, and/or by the lymphocyte to monocyte cell ratio or other accepted markers of cancer risk, heart disease risk as indicated by the lymphocyte to monocyte cell ratio, CD38-positive blood cell counts or percentages or other accepted markers of heart disease risk, hair color, glomerular filtration or other accepted markers of kidney function, epigenetic age, or other critical endpoints of aging as well as to reduce or prevent GH-induced or GH releaser-induced hyperinsulinemia.

BRIEF DESCRIPTION OF THE FIGURES

FIG. 4 shows that the lymphocyte to monocyte ratio, which increases as cancer and cardiovascular disease risks decrease, increases in proportion to the replacement of thymic fat with putatively functional thymic mass.

FIG. 5 provides evidence that the invention surprisingly reverses the aging of hair follicles, based on increased hair pigmentation over the course of treatment.

FIG. 6 provides evidence that the invention surprisingly restores thymotrophic hormones in a subset of aging men, based on correlated increases in both IL-7 and FGF-21 in these men.

FIG. 7 reveals a previously unknown phenomenon, i.e., that the CD4/CD8 cell ratio peaks in the face of a constant or an increasing dose of GH or rise in IGF-1, which enables a novel GH dosing regimen that can prevent the decline in CD4/CD8 ratio over time.

FIG. 8 provides the first evidence that the invention can reverse thymic involution in all men with normal age-related thymic involution, based on measurement of increased thymic fat-free fraction (TFFF).

FIG. 10 provides evidence that the invention reverses renal functional aging based on improving glomerular filtration over time.

FIG. 11 provides the first evidence that, surprisingly, the invention can reverse generalized aging, based on reduced biological age after treatment as measured by a well-accepted epigenetic aging clock.

FIG. 12 demonstrates that the invention can successfully suppress GH-induced hyperinsulinemia despite the increasing GH doses described in FIG. 1.

DETAILED DESCRIPTION OF THE INVENTION

Figure 1:
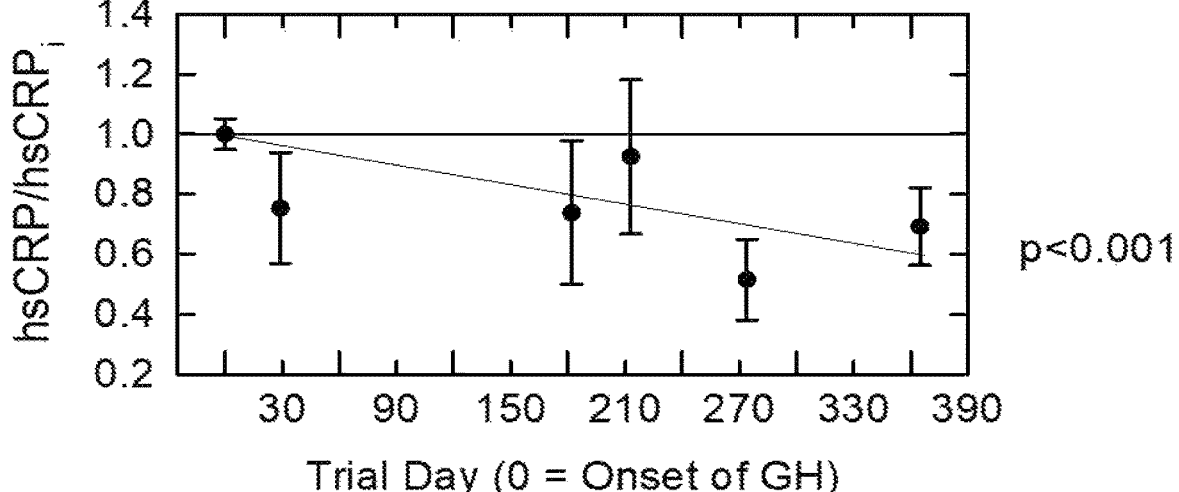
FIG. 1 provides evidence that the invention surprisingly reverses age-related inflammation ("inflammaging") based on reduced levels of the inflammatory marker, C-reactive protein (CRP) over time.

The invention consists of the use of a combination of human growth hormone (GH) and/or a GH releaser, dehydroepiandrosterone (DHEA), and metformin to manufacture a pharmaceutical dosage form to treat, prevent, or reverse broad aspects of human aging, including any one of, any combination of, or all of age-related changes in systemic inflammation as indicated by CRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced or GH releaser-induced hyperinsulinemia. The pharmaceutical dosage form or composition may consist of three separate agents or agent classes (the GH and/or GH releaser; DHEA; and metformin) administered simultaneously or within 2 hours of one another, or it may consist of GH and/or a GH releaser used simultaneously with or within two hours of a unified companion product composition containing DHEA in combination with metformin.

The invention is also a composition for use in the treatment of human aging, comprising a combination of GH and/or a GH releaser, dehydroepiandrosterone, and metformin whose administration results in mitigation of age-related changes in any one of, any combination of, or all of the following: systemic inflammation as indicated by CRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced or GH releaser-induced hyperinsulinemia. The composition may consist of three separate agents or agent classes (the GH and/or GH releaser; DHEA; and metformin) administered simultaneously or within 2 hours of one another, or it may consist of GH and/or a GH releaser used simultaneously with or within two hours of a unified companion product composition containing DHEA in combination with metformin.

The invention is also a method for the mitigation or reversal of human aging, comprising administering a combination of GH and/or a GH releaser, dehydroepiandrosterone, and metformin so as to result in mitigation or reversal of age-related changes in any one of, any combination of, or all of the following: systemic inflammation as indicated by CRP or other accepted markers, cancer risk as indicated by PSA levels or the percent of free PSA or the ratio of PSA to percent of free PSA or its reciprocal and/or by the lymphocyte to monocyte cell ratio, heart disease risk as indicated by the lymphocyte to monocyte cell ratio, CD38-positive blood cell counts or percentages, hair color, IL-7 levels, IL-21 levels, the CD4/CD8 cell ratio, naïve CD4 and/or CD8 cell numbers or percentages, total CD4 and/or CD8 T cell numbers or percentages, bone marrow density, thymic fat-free fraction, glomerular filtration, and epigenetic age, as well as to reduce or prevent GH-induced of GH releaser-induced hyperinsulinemia. The method may consist of administering three separate agents or agent classes (the GH and/or GH releaser; DHEA; and metformin) simultaneously or within 2 hours of one another, or it may consist of administering GH and/or a GH releaser simultaneously with or within two hours of the oral administration of a unified companion product composition containing DHEA in combination with metformin.

Suitable Medication Compositions

The utility of GH for the invention as reduced to practice is proven beyond doubt by the Examples described below. The purpose of administering GH is to increase circulating levels of both GH and IGF-1, which then modulate appropriate biological targets to produce the intended therapeutic effects. However, GH is costly, and alternative means are available for elevating circulating GH and IGF-1 so as to modulate the same biological targets as are modulated by GH and IGF1 and thereby to achieve the same biological effect as is achieved by GH injection. Therefore, any method, composition, or use of agents to manufacture a pharmaceutical dosage form that raises blood concentrations of GH and IGF-1 so as to produce the same therapeutic effect as GH injection within the practice of the present invention is an acceptable equivalent method, composition, or use to GH injection, GH, or GH use, respectively, for the purposes of the present invention.

Within the purposes of the present invention, "a GH releaser" or "GH releaser" is understood to mean either a single molecular entity (including complexes such as salts) or a combination of molecular entities whose administration results in an increase in circulating blood levels of GH and IGF-1 such that the resulting blood concentrations of GH and IGF-1 fall within the range of the concentrations that are reached (in individuals capable of increasing IGF-1 levels in response to GH injection) after GH is injected for the purposes of the present invention. However, it is not necessary to measure blood concentrations of GH for the purpose of determining the effectiveness of a GH releaser, because suitable increases in blood GH levels can be inferred from suitable increases in blood IGF-1 levels, and blood IGF-1 levels are conveniently measured, whereas GH levels are often awkward and costly to measure. The prior art has verified the release of GH by GH releasers, and there is no need to duplicate that verification in individuals. As long as the IGF-1 response to GH releaser administration is measured and is found to be satisfactory, use of the GH releaser is appropriate. For those individuals for whom the administration of a GH releaser does not result in an adequate increase in IGF-1, the use of GH is preferred over the use of a GH releaser for the purposes of the present invention. For purposes of evaluating the suitability of a GH releaser for use in this invention, a fold change in IGF-1 level of at least 1.2 fold, or a final IGF-1 concentration of at least 170 ng/ml, are indicative of at least the potential for an adequate response.

GH releasers are well known to those of skill in the art. Examples include but are not limited to:

sermorelin, ipamorelin, ghrelin, GHRH, and MK-0677.

In each case, the dose of GH releaser to be administered is equal to the dose required to optimize the CD4/CD8 cell ratio, which will be specific to each individual, using the dosing method described below.

In the prior art, GH releasers have been used as alternatives to the use of GH. However, a useful variation of part of our pharmaceutical composition is a combination of GH and a GH releaser. GH is ideally administered at bedtime, so as to simulate the normal diurnal elevation of IGF-1 that occurs during sleep, when the largest release of GH normally takes place. However, injection of recombinant GH (the preferred form of GH to be used in the present invention) may blunt the natural release of GH by the pituitary, thus both disturbing normal GH physiology and resulting in a need for a higher dose of GH than would be the case if natural GH release occurred. This problem can be overcome by combining GH and a GH releaser into a unified product composition using methods known in the art, or co-administering both GH and GH releaser as a virtual unified product, which can be marketed as one product. This approach and composition will be valuable when GH injection is generally preferred over the use of a GH releaser, but it is desired to reduce the cost of GH injection, and when the use of a GH releaser alone is able to raise IGF-1 levels but is insufficient to optimize the CD4/CD8 cell ratio. The approach will also be appealing to those who wish to combine the benefits of GH with the theoretical safety advantages of GH releasers.

In combinations of GH and GH releaser, the dose of GH will generally be reduced by 10-50% compared to non-use of a GH releaser, and the dose of GH releaser will generally be in the range of 30-100% the dose that would be administered without GH. Typically, GH and GH releaser preparations consist of a standardized amount of freeze-dried powder that is reconstituted to a liquid state prior to injection. A convenient unified dosage form can contain 50% as much GH per vial of powder as is normally present and 75% as much GH releaser as is normally present, with total delivered dose per injection being determined by the volume injected as required on an individualized basis.

The inclusion of both DHEA and metformin within the invention was discovered to be mandatory for optimum control of GH-induced hyperinsulinemia. Even though each agent was beneficial for suppressing hyperinsulinemia, neither agent alone was sufficient, and even in combination, it was necessary to employ the maximum permissible doses of each within the limits set by the trial design. Sulfonylureas and meglitinides, which increase insulin secretion, are inappropriate treatments for hyperinsulinemia.

DHEA and metformin can easily be combined into a single dosage form or composition because both are solids and will be chemically stable when combined. A unified composition of DHEA and metformin is advantageous for simplifying treatment, improving patient compliance, ensuring correct dosage administration, and adapting both DHEA and metformin pharmacokinetics to the purposes of the present invention. In particular, a significant deficiency of metformin and of lower doses of DHEA for the suppression of GH-induced hyperinsulinemia is the fact that the half-lives of these agents in the bloodstream are shorter than the expected duration of hyperinsulinemia. By incorporating DHEA and metformin into a timed-release formulation, which is easily done using technologies known to those of skill in the art, the antihyperinsulinemic effect of this combination of agents can be tailored to match the duration of the hyperinsulinemic effect of GH or a GH releaser. In general, release over 9-15 hours is desirable to either completely suppress hyperinsulinemia or enable hyperinsulinemia to be controlled during sleep so that a second dose of DHEA plus metformin can be administered in the morning to continue insulin suppression.

As described below, useful initial doses of DHEA and metformin are 75 mg and 850 mg, respectively, which may be combined into one dosage form containing these quantities. Ingesting two such tablets will deliver 150 mg of DHEA and 1700 mg of metformin, which are both useful doses during high to intermediate dosing with GH/GH releaser. At the highest doses of GH/GH releaser, three tablets comprising 225 mg of DHEA and 2550 mg of metformin can be ingested, either simultaneously or in divided doses taken within 2-4 hours of GH administration, including one tablet with dinner and two tablets at bedtime along with GH/GH releaser. This dosage form will be advantageous with or without timed release formulations; 225 mg of DHEA is projected to sustain elevated DHEA levels for over 9 hours, whereas the half-life of metformin is shorter and may justify selective time release of this agent. Of course, other variations are practicable within the invention, including a tablet containing only 33 or 50 mg of DHEA and 850 mg of metformin for men with initial PSA levels between 3 and 4 at the onset of the trial (these men can begin with 50 mg/850 mg and switch to two or three 33 mg/850 mg tablets as insulin suppression needs increase, so as to limit ultimate DHEA intake to 99 mg/dose), and a women's tablet that contains only 17 or 33 mg of DHEA and 850 mg of metformin, to limit the highest intake to 51 or 99 mg, respectively, when three tablets are consumed. Women can and should initiate treatment with the men's 50 mg DHEA plus 850 mg metformin tablet, and then switch to one of the other women's tablets when the number of tablets needed to suppress insulin levels increases to two or three.

The above formulations are designed particularly to combat nocturnal hyperinsulinemia and enable the user to awake with a normal insulin level despite taking antihyperinsulinemic therapy only once, prior to sleeping. However, they will be useful as well for daytime GH therapy, combining greater convenience with better insulin control overall. In fact, these companion formulations can be used by individuals who are taking metformin for type 2 diabetes, who may benefit from the inclusion of DHEA and timed release of metformin, without thymus regeneration or aging reversal therapy.

The inventors believe that the combination of GH or a GH releaser with DHEA and metformin creates an invention that is "more than the sum of its parts." For reasons that are not completely clear, the combination of these specific agents has beneficial effects that are otherwise not available. For example, as noted above, GH alone is generally expected to accelerate epigenetic aging rather than to reverse it, metformin use was not shown to either slow or reverse epigenetic aging in women [35], and there is no evidence that DHEA alone can reverse epigenetic aging, but the combination of agents comprising the present invention quite clearly does have this profound and unprecedented effect. As another example, one individual has reported that DHEA caused immediate and significant prostatic hypertrophy when used either alone or in combination with metformin, but when it was used in combination with both metformin and GH, prostatic hypertrophy was, surprisingly, actually reversed (made significantly less than prior to DHEA administration), and sexual function was also improved. Therefore, we do not believe that the totality of the effects of our invention would be obvious to one of ordinary skill in the art based on prior art knowledge. Accordingly, our results, methods, and medication compositions and combinations enable beneficial new treatments to improve human health and enable beneficial new drug indications.

Medication Doses and Medication Dose Administration

Best Mode GH/GH releaser Administration Method. The initial dose of GH for men is preferably in the range of 0.01-0.02 mg/kg, to enable pre-adaptation of the body to GH without side effects, preferably for 1-6 weeks. The initial dose of GH releaser is chosen to produce the same effect on IGF-1 levels as 0.01-0.02 mg/kg GH, as determined from prior art knowledge, and is also maintained for 1-6 weeks when a GH releaser is used in place of or in addition to GH. Postmenopausal women should be started on the same dose regimen whether or not they are taking estrogen replacement hormones (HRT). Women on HRT will experience lower increases in IGF-1, but lower increases in IGF-1 will enable more thorough evaluation of safety prior to increasing doses for thymus regeneration/aging reversal. Women should be carefully evaluated for breast cancer risk prior to enrolling in thymus regeneration/aging reversal treatment, including genetic testing for alleles that favor breast cancer development.

After the initial adaptation phase, the dose of GH, GH releaser, or GH plus GH releaser is increased so as to maximize the CD4 to CD8 cell ratio, as measured by commonly available blood testing services, over about the next 60 days in both men and women. Typically, a target CD4/CD8 ratio of 120±10% of baseline is considered satisfactory for 50-65 year-old men and women, regardless of the initial absolute CD4/CD8 ratio, and regardless of whether the ratio is increased by a decrease in CD8 cell counts or percentages or by an increase in CD4 cell counts or percentages (both ways of computing the CD4/CD8 cell ratio give similar results and are acceptable for purposes of the invention).

The preferred GH/GH releaser dosing frequency should be 4-7 times a week. Side effects should be controlled by reducing dosing frequency first and then, if that is insufficient, by dose reductions. A dosing frequency as low as 3 times a week can be effective for some patients.

We find that a maximum CD4/CD8 cell ratio is achieved in different individuals over a broad range of absolute IGF-1 concentrations and IGF-1 fold changes. The prior art method of increasing IGF-1 levels or inducing IGF-1 fold changes to either an arbitrary extent or as much as possible within upper physiological limits was found to be counterproductive, resulting in eventual decreases in the CD4/CD8 cell ratio. We also found wide variations in IGF-1 concentrations in response to a specific dose of GH, and essentially no correlation between CD4/CD8 cell ratio and IGF-1 concentration. Therefore, the optimum dosing strategy is to optimize CD4/CD8 cell ratio by either increasing or decreasing the GH/GH releaser dose as may be necessary as indicated by how the ratio changes with dose. This dose-response relationship may also change over time, so monitoring once every 1-3 months is recommended. Thus, medical supervision is necessary for achieving optimal results.

The strategy of dosing based on the CD4/CD8 ratio is unique, and is the first non-arbitrary method of GH/GH releaser administration. This method was inferred a posteriori based on the unprecedented observation that with the prior art method, the CD4/CD8 ratio tended to peak after different treatment times in different individuals, and then further decline, as described in detail below.

Because food and alcohol may inhibit natural HGH release from the pituitary, the effectiveness of GH in the present invention should be maximized by not drinking alcoholic or sugary beverages or consuming significant quantities of food within 2-4 hours of injecting GH.

Best Mode DHEA Administration Method. DHEA was not found to either raise testosterone levels (at doses up to 200 mg) or induce benign prostatic hypertrophy in the presence of GH or GH plus metformin in our trial. The best mode use is to administer DHEA within one or two hours, and ideally simultaneously, with the administration of GH. A useful initial oral dose of DHEA for most men, once GH treatment begins, is 75 mg. Men with PSA levels between 3 and 4 should restrict DHEA to 50 mg initially, and raise DHEA only if benign prostatic hypertrophy and/or PSA elevation is not encountered. Men with PSA levels above 4 should not undergo thymus regeneration/age reversal therapy unless PSA elevation is caused by established prostatitis or until additional information becomes available establishing the safety of treatment for such men. We believe that for most men, 300 mg of DHEA should be safe, but we recommend limiting DHEA intake to 225 mg until more safety information becomes available.

Women can safely take 50 mg of DHEA, and in the best mode, this is the preferred initial dose unless specific issues arise for particular women. Out of general caution, we recommend limiting the intake of DHEA to 100 mg for women. This can be achieved using the dosage forms described above, which ensure limitation of DHEA to 51 or 99 mg even when antihyperinsulinemic therapy is maximized.

Best Mode Metformin Administration Method. A useful initial dose of metformin, which should be given upon initial administration of GH, is 850 mg. If necessary to prevent gastric distress, this dose can be divided into two doses taken as close together in time as gastric distress will permit. Most individuals do not have difficulty taking this or higher doses of metformin. Metformin, like DHEA, can be taken either as part of a virtual composition or as part of a unified product composition containing both DHEA and metformin, as detailed above.

As for GH/GH releaser administration, the intake of metformin and DHEA should gradually increase over about the first 60 days of therapy to adjust to the continuously changing degree of insulin resistance induced by the GH/GH releaser. Thereafter, an additional, slower increase or decrease may be required, as GH/GH releaser dose is fine-tuned and the body adjusts to all three medications. The metformin dose ranges for men and women are the same. However, if women experience a different hyperinsulinemic effect than men, or a different antihyperinsulinemic effect of DHEA and metformin, dose adjustments can easily be made as necessary.

The metformin dose ranges described here differ significantly from ranges recognized in the prior art. The maximum accepted single dose of metformin is 850-1200 mg, and doses above 850 mg may cause an upset stomach in some users. However, in our experience, and as newly disclosed herein, 850-1200 mg of metformin is very insufficient to control hyperinsulinemia induced by GH in, as measured the morning after a GH dose (typically, at 8-10 am), even when DHEA is co-administered. We were able to use higher doses with minimal to no difficulty by devising the following dosing methods.

First, 500 mg of metformin can be given with dinner, and another 1000 mg can be co-administered with HGH and DHEA, achieving a total dose of 1500 mg. This regimen was universally well tolerated. Second, taking 1500 or 2000 mg of metformin in one dose together with GH at bedtime was also well tolerated, perhaps because the onset of sleep relieves feelings of gastric discomfort. Third, taking 1500 mg at dinner and 1000 mg with DHEA and HGH at bedtime was also well tolerated, enabling us to attain a dose of 2500 mg. In these methods, "dinner" need not be taken literally, the essence of the concept being to essentially administer a large virtual dose by combining two smaller doses that are administered within an effective time span, which may be 1-5 hours in duration, but preferably 1-2 hours in duration, to reduce side effects such as gastric distress while still enabling increased control of hyperinsulinemia.

Essentially, we learned that we could compensate for the short half-life of metformin in the bloodstream (~2-3 hours) by using quantities beyond normal dosing limits to prolong its effectiveness, and discovered that this was acceptable in all cases, perhaps in part because we administered GH at night to simulate the normal diurnal peak in GH that takes place shortly after the onset of sleep. However, the same goals can be achieved even more effectively by using the timed dose release preparation described herein, which will deliver metformin or metformin and DHEA over a longer time span, both reducing gastric distress and achieving longer-lasting protection from hyperinsulinemia. In addition, this preparation can also if desired be taken during the day without distress due to slower release of the metformin. Short Term Thymus Regeneration and Aging Reversal is Sufficient A unique feature of our treatment is that it need not and should not be implemented for the life of the patient in order to achieve life-long benefits. Once thymus regeneration has been established and new T cells have been produced and released into the circulation, they may persist for decades even though the thymus will re-involute following the termination of treatment. In addition, aging reversal, once shown to be long-lasting, might only need to be repeated once every few years, or less frequently. This feature of the present invention is advantageous for reasons of both safety and cost, and as further improvements of our invention are made, the duration of benefit may become longer still, and the duration of required treatment may become shorter. In the present best mode practice of the invention, we believe that the optimum treatment time is 0.5-1.5 years, and perhaps 0.75-1.25 years.

EXAMPLES

Nine normal, putatively healthy 50-65 year-old male volunteers with normal age-related thymic involution were enrolled in and completed a clinical study performed under an IND from the US Food and Drug Administration and separate supervision from a California Institutional Review Board. All aspects of the study also complied with the oversight requirements and standards of multiple institutions at Stanford University. The TRIIM trial (standing for Thymus Regeneration, Immunorestoration, and Insulin Mitigation) treatment period was limited to 12 months. Exclusion criteria included GH use in the prior 10 years, carpal tunnel syndrome, malignancies or high risk of malignancy, BMI greater than 30, PSA above the age-adjusted range, symptomatic prostatic hypertrophy, unstable metabolic disorders, unstable cardiovascular disorders, elevated levels of inflammatory markers, alcoholism, allergy to study medications, cognitive impairment, abnormal metabolic or hormonal results, existing type 1 or type 2 diabetes, or other unstable medical conditions. Informed consent was obtained from all patients and was collected using IRB-approved informed consent documents and procedures. The study was conducted consistently with the Declaration of Helsinki, Protection of Human Volunteers (21 CFR 50), Institutional Review Boards (21 CFR 56), and Obligations of Clinical Investigators (21 CFR 312).

Data variability was minimized and controlled by using each volunteer as his own control, and by standardizing the time and day of blood sampling. Blood was generally collected between 7 AM and 10 AM to avoid the effects of circadian and other temporal influences. In addition, patients standardized their pre-testing evening meal, used consistent testing sites and methods, and were redundantly tested between pre-established time points in some cases. All volunteers were asked to take supplements of 3000 IU vitamin $D_3$ and 50 mg of elemental zinc daily. Further, volunteers were instructed not to consume food or alcohol within 4 hours of medication administration.

The initial dose of GH was 0.015 mg/kg, injected subcutaneously into superficial abdominal fat using a provided "pen" injector designed for this purpose. GH doses were varied over the time course described above so as to maximize IGF1, and were not adjusted for any changes in body weight.

Insulin mitigation in the trial was staged to enable the effects first of DHEA and then of DHEA plus metformin to be evaluated. The course of dose adjustment of DHEA and metformin in the trial were as described above.

The following unexpected and remarkably beneficial new discoveries were made as a result of the TRIIM trial.

Example 1

As shown in FIG. 1, as the trial progressed and GH doses increased, there was a sustained trend for high-sensitivity CRP (hsCRP), a marker of systemic inflammation, to decrease. By 9-12 months, the decrease was about 40±10%, which is substantial, and the decline in hsCRP at 9-12 months was statistically significant compared to baseline (p<0.001). Normally, hsCRP would be expected to rise or stay the same over a one-year period, but with the treatment and medications of the invention, this normal age-related trend was reversed, despite attempted reactivation of the aging immune system. This contradicts the prior art concern that immune stimulation must exacerbate inflammation, and indicates that it is possible to simultaneously increase immune competence (see below) and decrease inflammation.

Example 2

Figure 2:
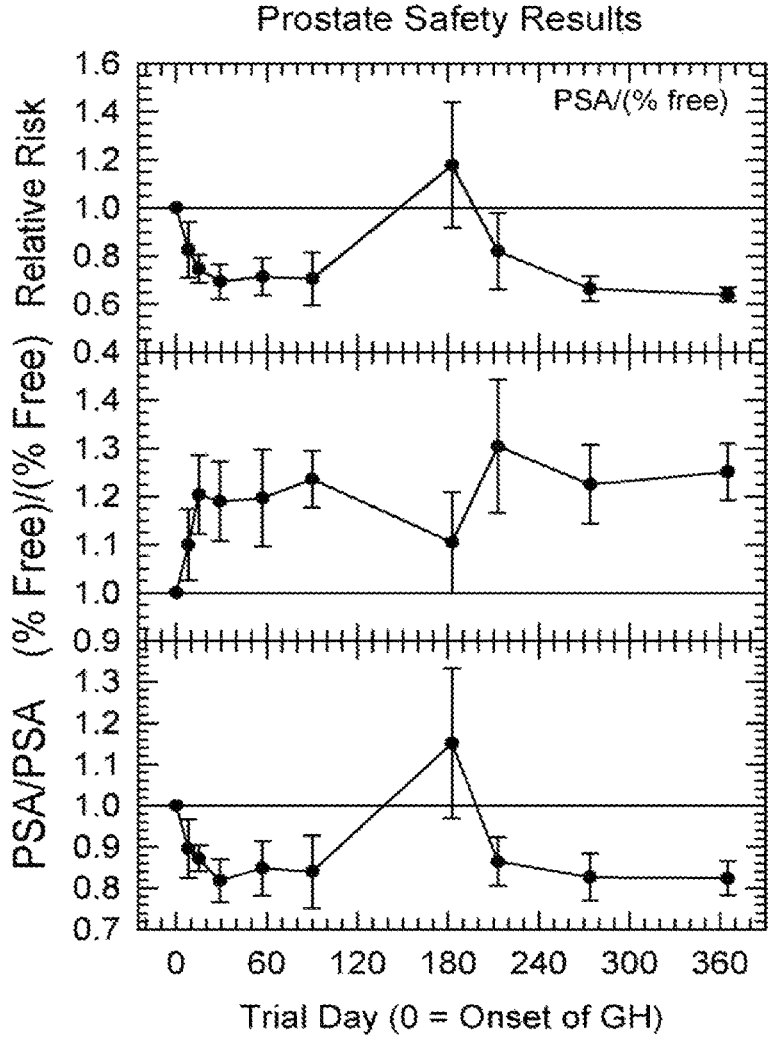
FIG. 2 provides evidence that the invention surprisingly reverses the age-related increase in prostate cancer risk based on reduced levels of prostate-specific antigen (PSA), increased percentages of free (unbound) PSA, and the ratio of PSA to free PSA.

FIG. 2 provides evidence that the medications of the invention surprisingly and rapidly (within 1 month) reverse the normal age-related increase in prostate cancer risk based on reduced levels of prostate-specific antigen (PSA, which rises with risk), increased percentages of free (unbound) PSA (with declines with increasing risk), and the ratio of PSA to free PSA, which was devised as an overall index of risk. Throughout most of the trial, relative risk is reduced by about 30%, and at 12 months, the risk factor decrease of nearly 40% was significant at the p<0.001 level. The increase in PSA, decrease in percent free PSA, and spike in putative overall risk at 6 months was due to results for three men. Given the immediate return to normal values after this time point (in the worst case, PSA was re-checked one week after the aberrant result, and was found to have returned to baseline levels, and in no case did the PSA level rise to 4 or above), the spike was not due to prostate cancer, and is believed to have been due to sexual activity too close to the time of blood collection.

The results of FIG. 2 are remarkable because they show a reduction in prostate cancer risk by a treatment that induces greatly increased IGF-1 levels, which have been considered a risk factor for prostate cancer, coupled with the use of an androgenic steroid. This effect on cancer risk is entirely unpredictable over the prior art and remains unexplained. Furthermore, the trend is strong enough to be clearly visible even in a group of only 9 rather heterogeneous aging men. Not visible in this figure is the fact that this trend applied without regard to baseline prostate cancer risk, men with PSA levels between 3 and 4 at the onset of the trial benefitting by the same proportion as men with PSA levels of 2 and below.

Example 3

Figure 3:
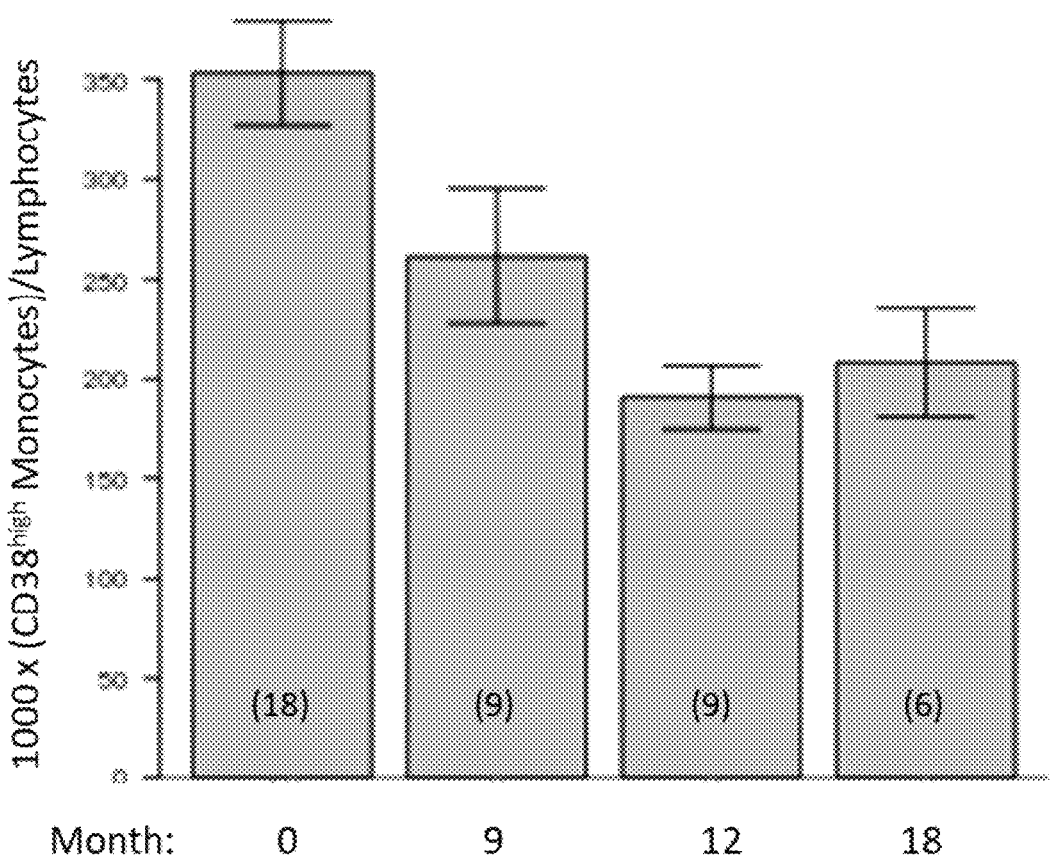
FIG. 3 provides evidence that the invention surprisingly reverses one of the most central drivers of aging in mammals, namely, the normal age-related reduction in cellular NAD levels, based on a reduced ratio of CD38-positive monocytes to lymphocytes. The same finding indicates substantially reduced general risk of cancer and cardiovascular disease.

FIG. 3 shows the ratio of circulating CD38 positive monocytes to total lymphocytes over the 12 months of the TRIIM trial and for another 6 months after discontinuing treatment. There is more than a 33% decline in the monocyte to lymphocyte ratio (MLR), which is quite significant, both biologically and statistically (p=0.00055), and this decline persists after discontinuing treatment. This is to be understood in the light of the fact that CD38 is the enzyme whose age-related increase in expression drives the cardinal age-related loss of NAD [8], which in turn drives deep and widespread aspects of mammalian aging [15]. An increased MLR also strongly correlates with the age-related increase in risk of both cancer and cardiovascular disease [22]. Cancer and cardiovascular disease are the two leading killers of aging humans, and reduced risk from these two diseases of aging further suggests a general reversal of aging processes. The MLR was determined from CyTOF analysis of TRIIM PBMC samples that were stored and analyzed at Stanford's Human Immune Monitoring Center.

Example 4

FIG. 4 shows the relationship between thymic fat-free fraction (TFFF; see below) and the lymphocyte to monocyte cell ratio (LMR). The statistical significance of the correlation is at the p=0.0019 level, and links the improvement in LMR to the improvement in putative thymic functional mass. In fact, when variance explained by changes in TFFF are factored out of variance in the LMR, no change in LMR survives, suggesting that changes in the LMR are in fact caused by improvements in thymic function.

Example 5

To our surprise, three of our trial volunteers (33%) reported to us that their wives and friends had noticed darkening of their hair. FIG. 5 provides evidence that the invention surprisingly reverses the aging of hair follicles, based on three before-and-after comparisons showing one volunteer's hair a few months before treatment and at the end of treatment. This result is all the more remarkable considering that hair whitening is caused by the death of follicular melanocyte stem cells, suggesting restoration of stem cells by the invention.

These observations were completely unanticipated. This phenomenon is suggestive of a broad "anti-aging" effect, and has not been reported to our knowledge after use of any of the individual agents of the present invention (in this case, GH, DHEA, and metformin) when they are not combined with one another as required by the present invention, and this effect of the combination is unpredictable from the properties of the uncombined agents. The phenomenon adds further market appeal to the treatment, manufacturing process, medication combination, and compositions of the present invention.

Example 6

FIG. 6 provides evidence that the invention surprisingly restores thymotrophic hormones in a subset of TRIIM trial volunteers, based on correlated increases in both IL-7 and IL-21 (FGF-21) in these men. IL-7 is a hormone whose downregulation in youth has been associated with the onset of thymic involution, and restoration of which has been proposed, but not achieved, for inducing thymic regeneration [5]. IL-21 has been shown to regenerate the aged thymus in rodents when excessively over-expressed to a level that may or may not be feasible or desirable in humans [2, 47], and is a theoretical alternative pathway to thymus regeneration. We asked whether part of the mechanism of action of our invention was induction of IL-7 and/or IL-21, i.e., stimulation by our medication combination of endogenous thymic regeneration pathways. FIG. 6 indicates that the answer to the question is positive, and demonstrates a heretofore unknown and safe method for increasing IL-7 and IL-21 in humans. Once again, reactivation of pathways found in youth provides additional evidence for an overall aging reversal effect of our combination of medications.

Example 7

FIG. 7 reveals a heretofore unknown phenomenon, i.e., that the CD4/CD8 cell ratio peaks in the face of a constant or an increasing dose of GH or rise in IGF-1, and thereafter declines. Different men show a peak in CD4/CD8 ratio at different times (here, 3, 6-9, and 12 months; one volunteer failed to respond at any time). The decline of CD4/CD8 cell ratio with aging is a classical indication of the "immune risk phenotype" or immunosenescence, and appears to occur with or without chronic viral exposure and has been a strong predictor of the short-term risk of death [37]. Our results therefore indicate that prior art methods of regenerating the thymus require improvement. Without knowledge of the phenomenology of FIG. 7, it was impossible to optimize GH therapy during the TRIIM trial, and in fact, the phenomenon was not understood until after the end of the trial, but we can now infer that the GH dose should stop increasing, and should even begin to decrease, when the CD4/CD8 cell ratio is observed to peak, so that the peak can be sustained. Although the considerable successes of the TRIIM trial were achieved without the advantage of the teachings of FIG. 7, adjusting treatment according to the findings of FIG. 7, as described herein, should produce still stronger benefits.

Example 8

FIG. 8 provides detailed information on the improvement in functional thymic mass achieved by the TRIIM trial protocol and medications, as inferred from a reduction in the thymic fat percentage (TFFF=thymic fat-free fraction=100 minus the percentage of thymic mass represented by fat, where the thymic fat fraction was computed using an algorithm that has been shown to be of higher accuracy than standard histopathological assessment by biopsy [21]). Two basic phenomena are seen. First, for most men, there was a steady replacement of thymic fat with putative thymic functional mass from 0 to 9 months of treatment. In some cases, this improvement continued, whereas in others, it appeared to regress slightly from 9 to 12 months, akin to the peaking of the CD4/CD8 cell ratio described in FIG. 7, and perhaps originating from the same preventable cause. Second, two exceptional individuals showed a different pattern: their baseline TFFF was abnormally high and showed little improvement over time. These findings are further referred to in conjunction with the discussion of FIG. 9 below.

Example 9

Figure 9:
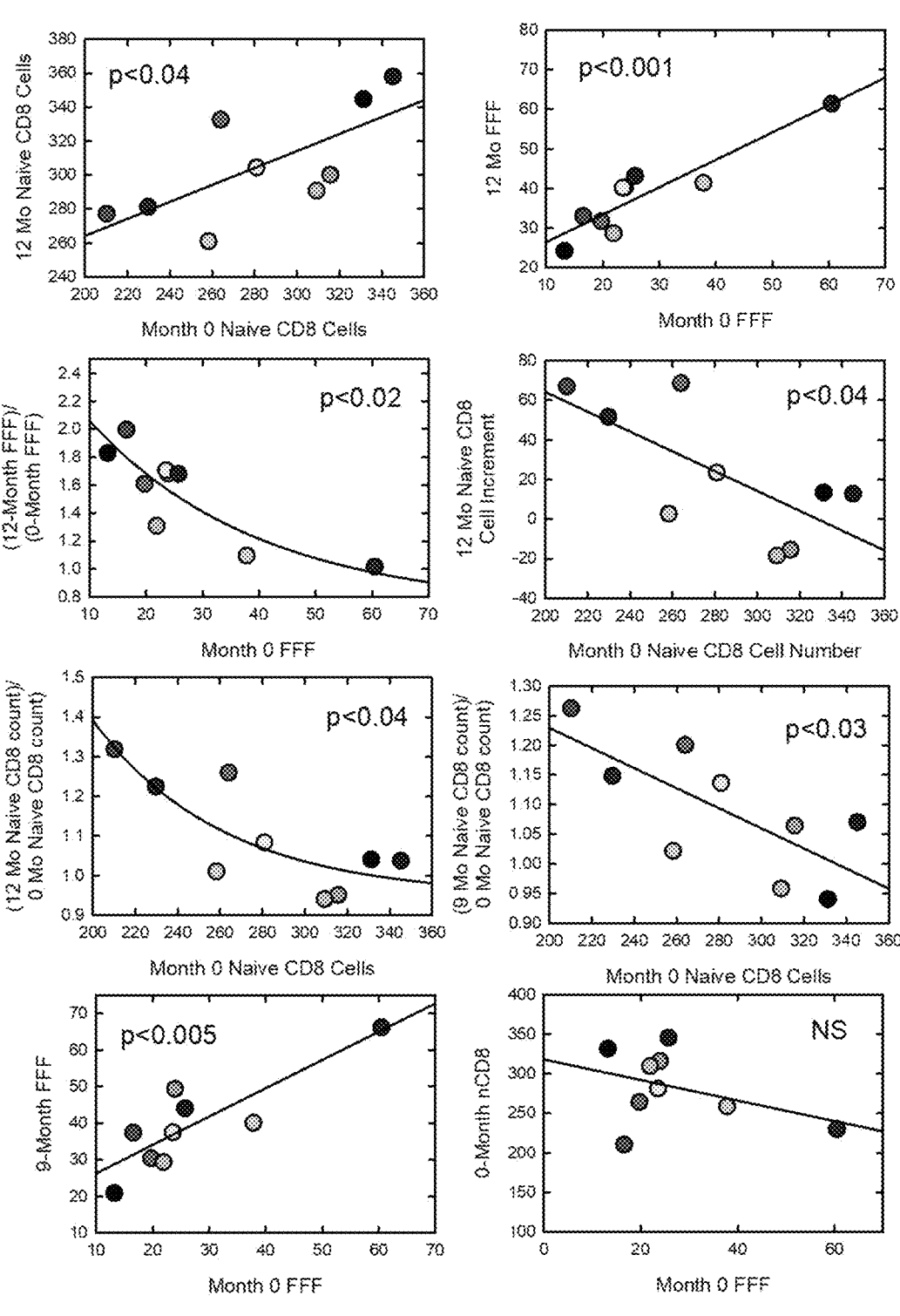
FIG. 9 provides evidence that the invention successfully improves T cell populations in a subset of aging men and that the subset of men who benefit can be predicted prior to treatment.

FIG. 9 provides a glimpse of some of the evidence that the invention is able to improve T cell populations in at least a subset of aging men and that the subset of men who benefit can be predicted prior to treatment and is closely related to changes seen in the thymus. As can be seen, the relative improvement of TFFF depends on basal TFFF: the higher the TFFF at baseline, the less room there is for improvement. Similarly, the improvement of naïve CD8 cell counts also depends on how high the counts are at baseline: volunteers with high naïve CD8 cell numbers at baseline have less need for improvement, and show less improvement, but despite lack of improvement, absolute counts remain good. Also, like TFFF, naïve CD8 cell counts are sometimes lower at 12 months than at 9 months in some cases, whereas volunteers with lower naïve CD8 cell counts at baseline, who have a stronger need for improved counts, show continuing improvement between 9 and 12 months. These results represent only a partial analysis of the TRIIM data; additional analysis is likely to show additional evidence of benefit. Note that the lower right panel shows that TFFF and naïve CD8 cells don't correlate well at baseline; therefore, changes in TFFF and naïve CD8 cells can only be correlated by showing the same trends in both, as demonstrated here.

In addition to the data shown here, there is a way to infer naïve CD8 cell counts from epigenetic clock data, which may be more accurate than relying on a relatively small number of frozen-thawed cell samples. On the basis of such data, the p value for an overall increase in naïve CD8 cell counts was found to be p=0.0017. A similar analysis for naïve CD4 cells fell just short of statistical significance, but subgroup analysis of the kind shown for naïve CD8 cells in
FIG. 9, now underway, may reveal subsets of volunteers
whose improvements in naïve CD4 cells are clear.

The fact that thymic structural improvement, the CD4/
CD8 cell ratio, and naïve CD8 T cells all show signs of
improvement to a certain point followed by a small rever-
sion toward baseline supports the significance of adjusting
treatment based on the CD4/CD8 cell ratio so as to prevent
overdosing and desensitization of the thymus.

Meanwhile, the observations of FIG. 9 provide valuable
diagnostic criteria (TFFF and naïve CD8 cell counts) by
which patients wishing to consider thymus regeneration and
aging reversal treatment can be evaluated prior to treatment
to determine their likelihood of experiencing a positive
response.

Finally, the restoration of naïve CD8 and perhaps naïve
CD4 T cells represents yet one more example of processes
that are the opposite of normal age-related trends.

Example 10

We observed that the treatment medications and methods
were able to reverse age-related fatty infiltration of the bone
marrow, based on the same analytical method used to
determine an improvement in TFFF. The p value for this
change was $9.5 \times 10^{-12}$. Bone marrow function in aging is
important for many reasons, but one important reason is that
the bone marrow supplies progenitor T cells to the thymus,
where they mature into competent T cells in youth. Suc-
cessful immunorestoration in the elderly requires appre-
ciable bone marrow function, and the changes observed
from MRI investigation of bone marrow indicate that the
medications of the present invention have effects on bone
marrow consistent with this requirement. This change is one
more change that is contrary to the direction of normal aging
trends.

Example 11

FIG. 10 shows that the medications and treatments of the
present invention result in increased glomerular filtration
rates over the course of the 12 months of treatment and
beyond, reaching statistical significance at 9 months, 12
months and overall out to 18 months. "eGFR" is "estimated
GFR" and is calculated based on age, sex, race, and serum
creatinine levels. Normally, renal function declines with
aging. Here is another example of the functional reversal of
a normal age-related trend.

Example 12

FIG. 11 demonstrates the first direct evidence for a global
reversal of human aging. Using an epigenetic clock licensed
by Zymo Research [20], the longitudinal epigenetic age of
TRIIM trial volunteers was calculated at months 0, 9, and
12. At baseline (month 0), the mean epigenetic age of the
volunteers was about 0.75 years older than their chronologi-
cal ages. By 9 months, there was a gain of about 0.8 years,
indicating rejuvenation back to a biological age appropriate
for the volunteers' mean chronological age. However, three
months later, the mean epigenetic age had declined to 1.5
years younger than the volunteers' mean chronological age.
In total, net rejuvenation after 1 year of treatment was about
2.25 years. But since 1 year of treatment would have
normally entailed one additional year of aging, the net gain
was actually 3.25 years compared to no treatment. The p
value for this change was 0.0059. In general, epigenetic clocks of this kind can determine biological age more
accurately than biological age can be estimated from
chronological age.

Example 13

FIG. 12 demonstrates that the invention can successfully
suppress GH-induced hyperinsulinemia despite the increas-
ing GH doses described in FIG. 1. Here, for context, insulin
blood levels are expressed as a fraction of the distance from
the bottom of the normal range to the top of the normal
range. Although insulin control was not perfect, the final
increase in insulin at trial end was acceptable based on
volunteers averaging about one fifth of the upper limit for
insulin. Note the rise in insulin early on, as lower doses of
GH were given without administration of DHEA or met-
formin, followed by declining insulin levels as antihyperin-
sulinemic therapy was begun. Insulin and the normal insulin
range were as reported by Quest Diagnostics.

SUMMARY

The present invention provides for the first time medica-
tion combinations, compositions, doses, dosage regimens,
and other methods that have demonstrable and objective
benefits for the treatment of immunosenescence and many
fundamental aspects of aging in human patients, and for
further improvements that are now enabled by the present
disclosures.

Additional ways to describe the invention include the
following.

1. A method whereby the co-administration of human
   growth hormone and/or one or more human growth
   hormone releasing agents, DHEA, and metformin to
   humans results in the reversal of age-related health risk
   factors other than thymic involution.
2. The method above ("the method") wherein the dose of
   human growth hormone or growth hormone releasing
   agents is adjusted in response to changes in the CD4 to
   CD8 T cell ratio so as to prevent the CD4 to CD8 T cell
   ratio from declining due to over- or under-administra-
   tion of human growth hormone or growth hormone
   releasing agents.
3. The method, wherein one age-related health risk factor
   that improves is the age-related decrease of estimated
   or directly measured glomerular filtration rate.
4. The method, wherein one age-related health risk factor
   that improves is the age-related increase in the blood
   level of prostate-specific antigen (or PSA) and/or the
   age-related decrease in the percent of free PSA.
5. The method, wherein one age-related health risk factor
   that improves is systemic inflammation, where the
   improvement is indicated by a decrease in high-sensi-
   tivity C-reactive protein (hsCRP) blood levels.
6. The method, wherein one age-related health risk factor
   that improves is the risk of cardiovascular disease,
   where the improvement is indicated by an increased
   lymphocyte to monocyte ratio.
7. The method, wherein one age-related health risk factor
   that improves is the risk of cancer, where the improve-
   ment is indicated by an increased lymphocyte to mono-
   cyte ratio.
8. The method, wherein one age-related health risk factor
   that improves is the age-related increase in CD38
   levels, where the improvement is indicated by a
   decrease in CD38 positive monocytes.

9. The method, wherein said co-administration of human growth hormone and/or one or more human growth hormone releasing agents, DHEA, and metformin to humans also results in increased hair pigmentation.

10. The method, wherein said co-administration of human growth hormone and/or one or more human growth hormone releasing agents, DHEA, and metformin to humans also results in increased blood levels of FGF21/IL21 and/or IL7.

11. The method, wherein the dose of DHEA is 17-300 mg.

12. The method, wherein the dose of metformin is 500 to 2500 mg.

13. The method, wherein metformin or metformin and DHEA are provided in a unified composition.

14. The method, wherein said unified composition of metformin and DHEA is provided in a timed-release dosage form for better matching the half-lives of DHEA and/or particularly metformin to the duration of the hyperinsulinemic effect of GH, GH releaser, or GH plus GH releaser.

15. The method, wherein said human growth hormone and/or one or more human growth hormone releasing agents are combined into a unified product composition.

As noted above, a major mode of biological action within the invention is elevation of IGF-1, which may be accomplished by any IGF-1 elevating agent, including the anabolic agent IGF-1 itself or a combination of IGF-1 and IGFBP-3. In addition, other insulin-mitigating agents besides DHEA and metformin may have utility in the invention, including as weak and secondary antihyperinsulinemic agents, such as cinnamon preparations, chromium picolinate, and other forms known in the art. The best mode reduction of the invention as described here is intended to be descriptive but not limiting, and may affect other critical endpoints of aging in addition to those described herein.

REFERENCES

1. Abs, R., Bengtsson, B. A., Hernberg-Stahl, E., Monson, J. P., Tauber, J. P., Wilton, P. and Wuster, C., *GH replacement in 1034 growth hormone deficient hypopituitary adults: demographic and clinical characteristics, dosing and safety*. Clin Endocrinol (Oxf), 1999. 50: p. 703-713.

2. Al-Chami, E., Tormo, A., Pasquin, S., Kanjarawi, R., Ziouani, S. and Rafei, M., *Interleukin-21 administration to aged mice rejuvenates their peripheral T-cell pool by triggering de novo thymopoiesis*. Aging Cell, 2016. 15(2): p. 349-360.

3. Anonymous, Humatrope, in *Physician's Desk Reference*. 2008, Thomson Healthcare: Montvale. p. 1823-1827.

4. Anson, R. M., Guo, Z., de Cabo, R., lyun, T., Rios, M., Hagepanos, A., Ingram, D. K., Lane, M. A. and Mattson, M. P., *Intermittent fasting dissociates beneficial effects of dietary restriction on glucose metabolism and neuronal resistance to injury from calorie intake*. Proceedings of the National Academy of Science, 2003. 100: p. 6216-6220.

5. Aspinall, R. and Mitchell, W., *Maintenance and restoration of immune system function*, in *The Future of Aging: Pathways to Human Life Extension*, G. M. Fahy, et al., Editors. 2010, Springer Science: Berlin Heidelberg New York. p. 489-520.

6. Attarwala, H., TGN1412: *From discovery to disaster*. J Young Pharm, 2010. 2(3): p. 332-336.

7. Bartke, A., *Growth hormone and aging. Endocrine*, 1998. 8: p. 103-108.

8. Camacho-Pereira, J., Tarrago, M. G., Chini, C. C. S., Nin, V., Escande, C., Warner, G. M., Puranik, A. S., Schoon, R. A., Reid, J. M., Galina, A., and Chini, E. N., *CD38 dictates age-related NAD decline and mitochondrial dysfunction through a SIRT3-dependent mechanism*. Cell Metabolism, 2016. 23(6): p. 1127-1139.

9. Creighton, C. J., Casa, A., Lazard, Z., Huang, S., Tsimelzon, A., Hilsenbeck, S. G., Osborne, C. K. and Lee, A. V., *Insulin-like growth factor-1 activates gene transcription programs strongly associated with poor breast cancer prognosis*. J Clin Oncol, 2008. 26(25): p. 4078-4085.

10. Everitt, A., *The effect of pituitary growth hormone on the aging male rat*. J Gerontol, 1959. 14: p. 415-424.

11. Fahy, G. M., Growth hormone therapy and related methods and pharmaceutical compositions, in U.S. Pat. No. 6,297,212 B1. 2001.

12. Fahy, G. M., *Apparent induction of partial thymic regeneration in a normal human subject: a case report*. Journal of anti-aging medicine, 2003. 6: p. 219-227.

13. Fahy, G. M., *Precedents for the biological control of aging: experimental postponement, prevention, and reversal of aging processes*, in *The Future of Aging: Pathways to Human Life Extension*, G. M. Fahy, et al., Editors. 2010, Springer: New York. p. 127-223.

14. Franceschi, C., Bonafe, M., Valensin, S., Olivieri, F., de Luca, M., Ottaviani, E. and Benedictis, G., *Inflammaging: An evolutionary perspective on immunosenescence*. Ann N Y Acad Sci, 2000. 908: p. 244-254.

15. Gomes, A. P., Price, N. L., Ling, A. J., J, M. J., Montgomery, M. K., Rajman, L., White, J. P., Teodoro, J. S., Wrann, C. D., Hubbard, B. P., Mercken, E. M., Palmeira, C. M., de Cabo, R., Rolo, A. P., Turner, N., Bell, E. L., and Sinclair, D. A., *Declining NAD(+) induces a pseudohypoxic state disrupting nuclear-mitochondrial communication during aging*. Cell, 2013. 155(7): p. 1624-1638.

16. Greenstein, B. D., Fitzpatrick, F. T., Kendall, M. D. and Wheeler, M. J., *Regeneration of the thymus in old male rats treated with a stable analogue of LHRH*. J Endocrinol, 1987. 112: p. 345-350.

17. Greenstein, B. D., de Bridges, E. F. and Fitzpatrick, F. T. A., *Aromatase inhibitors regenerate the thymus in aging male rats*. Int J Immunopharmacol, 1992. 14: p. 541-553.

18. GrowthHormoneResearchSociety, *Critical evaluation of the safety of recombinant human growth hormone administration: Statement from the Growth Hormone Research Society*. J Clin Endocrinol Metab, 2001. 86: p. 1868-1870.

19. Holtzenberger, M., Dupont, J., Ducos, B., Leneuve, P., Geloen, A., Even, P. C., Cervera, P. and Le Bouc, Y., *IGF-1 receptor regulates lifespan and resistance to oxidative stress in mice*. Nature, 2003. 421: p. 182-187.

20. Horvath, S., *DNA methylation age of human tissues and cell types*. Genome Biol, 2013. 14(10): p. R115.

21. Hu, H. H., Nayak, K. S. and Goran, M. I., *Assessment of abdominal adipose tissue and organ fat content by magnetic resonance imaging*. Obes Rev, 2011. 12(5): p. e504-e515.

22. Ji, H., Li, Y., Fan, Z., Zuo, B., Jian, X., Li, L. and Liu, T., *Monocyte/lymphocyte ratio predicts the severity of coronary artery disease: a syntax score assessment*. BMC Cardiovasc Disord, 2017. 17: p. 90.

23. Kalu, D. N., Orhii, P. B., Chen, C., Lee, D. Y., Hubbard, G. B., Lee, S. and Olatunji-Bello, Y., *Aged-rodent models of long-term growth hormone therapy: lack of deleterious effect on longevity*. J Gerontol A Biol Sci Med Sci, 1998. 53: p. B452-B463.

24. Kananen, L., Marttila, S., Nevalainen, T., Kummola, L., Junttila, I., Mononen, N., Kahonen, M., Raitakari, O. T., Hervonen, A., Jylha, M., Lehtimaki, T., Hurme, M., and Jylhava, J., *The trajectory of the blood DNA methylome ageing rate is largely set before adulthood: evidence from two longitudinal studies*. Age (Dordr), 2016. 38(3): p. 65.

25. Kelley, K. W., Brief, S., Westly, H. J. and al, e., *GH3 pituitary adenoma cells can reverse thymic aging in rats*. Proceedings of the National Academy of Science, 1986. 83: p. 5663-5667.

26. Khansari, D. N. and Gustad, T., *Effecs of long-term, low-dose growth hormone therapy on immune function and life expectancy of mice*. Mechanisms of ageing and development, 1991. 57: p. 87-100.

27. Li, W., Tao, L., Zhang, L. and Xiu, D., *Prognostic role of lymphocyte to monocyte ratio for patients with pancreatic cancer: a systematic review and meta-analysis*. Onco Targets Ther, 2017. 10: p. 3391-3397.

28. Longo, V. D. and Fabrizio, P., *Regulation of longevity and stress resistance: a molecular strategy conserved from yeast to humans?* Cell Mol Life Sci, 2002. 59(6): p. 903-908.

29. Longo, V. D. and Finch, C. E., *Evolutionary medicine: from dwarf model systems to healthy centenarians?* Science, 2003. 299: p. 1342-1346.

30. Marcus, R., Butterfield, G., Holloway, L. and al., e., *Effects of short-term administration of recombinant human growth hormone to elderly people*. J Clin Endocrinol Metab, 1990. 70: p. 519-527.

31. Masternak, M. M., Panici, J. A., Bonkowski, M. S., Hughes, L. F. and Bartke, A., *Insulin sensitivity as a key mediator of growth hormone actions on longevity*. J Gerontol Biol Sci, 2009. 64A(5): p. 516-521.

32. McCune, J. M., Loftus, R., Schmidt, D. K. and al., e., *High prevalence of thymic tissue in adults with human immunodeficiency virus-1 infection*. J Clin Invest, 1998. 101: p. 2301-2308.

33. Napolitano, L. A., Lo, J. C., Gotway, M. B. and al, e., *Increased thymic mass and circulating naive CD4 T cells in HIV-1-infected adults treated with growth hormone*. AIDS, 2002. 15: p. 1103-1111.

34. Napolitano, L. A., Schmidt, D., Gotway, M. B., Ameli, N., Filbert, E. L., Ng, M. M., Clor, J. L., Epling, L., Sinclair, E., Baum, P. D., Li, K., Killian, M. L., Bacchetti, P., and McCune, J. M., *Growth hormone enhances thymic function in HIV-1-infected adults*. J Clin Invest, 2008. 118: p. 1085-1098.

35. Quach, A., Levine, M. E., Tanaka, T., Lu, A. T., Chen, B. H., Ferrucci, L., Ritz, B., Bandinelli, S., Neuhouser, M. L., Beasley, J. M., Snetselaar, L., Wallace, R. B., Tsao, P. S., Absher, D., Assimes, T. L., Stewart, J. D., Li, Y., Hou, L., Baccarelli, A. A., Whitsel, E. A., and Horvath, S., *Epigenetic clock analysis of diet, exercise, education, and lifestyle factors*. Aging (Albany, NY), 2017. 9(2): p. 419-446.

36. Renehan, A. G., Zwahlen, M., Minder, C., O'Dwyer, S. T., Shalet, S. M. and Egger, M., *Insulin-like growth factor (IGF)-1, IGF binding protein-3, and cancer risk: systematic review and meta-regression analysis*. The Lancet, 2004. 363: p. 1346-1353.

37. Roberts-Thomson, I., Whittingham, S., Youngschaiyd, U. and al, e., *Aging, immune response and mortality*. Lancet, 1974. 2: p. 368-370.

38. Scanes, C. G., *Growth hormone action: carbohydrate metabolism, in Growth Hormone*, S. Harvey, C. G. Scanes, and W. H. Daughaday, Editors. 1995, CRC Press: Boca Raton. p. 371-377.

39. Scholz, M. C., Groom, M. K., Kaddis, A. J., Strum, S. B., Jennrich, R. I., Bahn, D. K., Chang, P. J., Becker, L. K. and Lam, R. Y., *Primary androgen deprivation (AD) followed by active surveillance (AS) for newly diagnosed prostate cancer (PC): A retrospective study*. Prostate, 2013. 73(1): p. 83-88.

40. Spencer, N. F. L., Poynter, M. E., Hennebold, J. D., Mu, H.-H. and Daynes, R. A., *Does DHEAS restore immune competence in aged animals through its capacity to function as a natural modulator of peroxisome activities?* Annals of the New York Academy of Science, 1995. 774: p. 200-216.

41. Steger, R. W., Bartke, A. and Cedim, M., *Premature ageing in transgenic mice epressing different growth hormone genes*. J Reprod Fertil Suppl, 1993. 46: p. 61-75.

42. Svensson, J. and Bengtsson, B. A., *Safety aspects of GH replacement*. Eur J Endocrinol, 2009. 161 (Suppl. 1): p. S65-S74.

43. Tatar, M., Bartke, A. and Antebi, A., *The endocrine regulation of aging by insulin-like signals*. Science, 2003. 299: p. 1346-1351.

44. Vermeulen, A., *Dehydroepiandrosterone sulfate and aging*. Ann N Y Acad Sci, 1995. 774: p. 121-127.

45. Wanagat, J., Allison, D. B. and Weindruch, R., *Caloric intake and aging: mechanisms in rodents and a study in nonhuman primates*. Toxicol Sci, 1999. 52(2 suppl): p. 35-40.

46. Weiss, E. P., Villareal, D. T., Fontana, L., Han, D.-H. and Holloszy, J. O., *Dehydroepiandrosterone (DHEA) replacement decreases insulin resistance and lowers inflammatory cytokines in aging humans*. Aging, 2011. 3(5): p. 533-542.

47. Youm, Y. H., Horvath, T. L., Mangelsdorf, D. J., Kliewer, S. A. and Dixit, V. D., *Prolongevity hormone FGF21 protects against immune senescence by delaying age-related thymic involution*. Proc Natl Acad Sci USA, 2016. 113(4): p. 1026-1031.

48. Yuan, R., Tsaih, S. W., Petkova, S. B., Marin de Evsikova, C., Xing, S., Marion, M. A., Bogue, M. A., Mills, K. D., Peters, LL, Bult, C. J., Rosen, C. J., Sundberg, J. P., Harrison, D. E., Churchill, G. A., and Paigen, B., *Aging in inbred strains of mice: study design and interim report on median lifespans and circulating IGF1 levels*. Aging Cell, 2009. 8(3): p. 277-287.

We claim:

1. A method for the reversal of human aging, comprising administering a growth hormone (GH) releaser, dehydroepiandrosterone (DHEA), and metformin so as to result in at least one of reduced epigenetic age, reduced prostate specific antigen (PSA), increased percentage of free PSA, increased ratio of free PSA to total PSA, lowered C-reactive protein (CRP) levels, increased hair color, increased IL-7 levels, and increased FGF-21 levels, wherein the GH releaser increases IGF-1 levels by at least 20% or to at least 170 ng/ml, and the GH releaser, DHEA, and metformin are administered simultaneously or within two to four hours of one another; and the GH releaser is selected from sermorelin, ipamorelin, ghrelin, and growth hormone releasing hormone (GHRH).

2. The method of claim 1, wherein the DHEA and metformin are administered in a unified companion product composition containing DHEA in combination with metformin wherein the GH releaser is administered simultaneously with or within 2-4 hours of the administration of the unified companion product composition containing DHEA in combination with metformin.

3. The method of claim 1, further comprising administering growth hormone (GH) simultaneously with the administration of said GH releaser, DHEA, and metformin, or within two hours of one another.

4. The method of claim 2, further comprising administering GH simultaneously with or within 2-4 hours of the administration of the unified companion product composition containing DHEA in combination with metformin.

5. The method of any one of claims 2 and 4, wherein said unified companion product composition containing DHEA in combination with metformin is a timed-release formulation.

6. The method of any one of claims 1-4, wherein the GH releaser, DHEA, and metformin are administered within two hours of one another.

7. The method of any one of claims 3 and 4, wherein the GH is administered within two hours of the administration of the unified companion product composition containing DHEA in combination with metformin.

8. A method for the reversal of human aging, comprising administering a growth hormone (GH) releaser, dehydroepiandrosterone (DHEA), and metformin so as to result in at least one of reduced epigenetic age, reduced prostate specific antigen (PSA), increased percentage of free PSA, increased ratio of free PSA to total PSA, lowered C-reactive protein (CRP) levels, increased hair color, increased IL-7 levels, and increased FGF-21 levels, wherein:

the GH releaser increases IGF-1 levels by at least 20% or to at least 170 ng/ml and the GH releaser, DHEA, and metformin are administered simultaneously or within two to four hours of one another; and the GH releaser is MK-0677.

9. The method of claim 8, wherein the DHEA and metformin are administered in a unified companion product composition containing DHEA in combination with metformin, wherein the GH releaser is administered simultaneously with or within 2-4 hours of the administration of the unified companion product composition containing DHEA in combination with metformin.

10. The method of claim 8, further comprising administering growth hormone (GH) simultaneously with the administration of said GH release, DHEA, and metformin, or within two hours of one another.

11. The method of claim 9, further comprising administering GH simultaneously with or within 2-4 hours of the administration of the unified companion product composition containing DHEA in combination with metformin.

\*    \*    \*    \*    \*